United States Patent [19]
Evans et al.

[11] Patent Number: 4,749,649
[45] Date of Patent: Jun. 7, 1988

[54] MICROBIAL Δ1-DEHYDROGENATION PROCESS USING A SCAVENGER OF TOXIC OXYGEN

[75] Inventors: Timothy W. Evans, Park; Leo A. Kominek, Portage; Holly J. Wolf, Comstock Township, Kalamazoo County; Sheryl L. Henderson, Portage, all of Mich.

[73] Assignee: The Upjohn Company, Kalamazoo, Mich.

[21] Appl. No.: 494,747

[22] Filed: May 16, 1983

[51] Int. Cl.⁴ .............................................. C12P 33/02
[52] U.S. Cl. ...................................................... 435/61
[58] Field of Search ........................................... 435/61

[56] References Cited
U.S. PATENT DOCUMENTS

| | | | |
|---|---|---|---|
| 2,837,464 | 6/1958 | Nobile | 195/51 |
| 3,047,469 | 7/1962 | Sih et al. | 195/51 |
| 3,091,575 | 5/1963 | Feldman et al. | 195/51 |
| 3,567,586 | 3/1971 | Soli | 435/27 |
| 3,751,340 | 8/1973 | Witz | 435/27 |
| 4,035,236 | 7/1977 | Wovcha | 195/51 |
| 4,041,055 | 8/1977 | Shephard et al. | 260/397.3 |

FOREIGN PATENT DOCUMENTS 1555004 11/1979 United Kingdom .

OTHER PUBLICATIONS

Methods in Enzymology, 4, 329–336, Quastel, J. H. (1957).
Biotech. & Bioengin., 20, 17–25, Yang, H. S. et al. (1978).

Primary Examiner—Alvin E. Tanenholtz
Attorney, Agent, or Firm—Roman Saliwanchik; Bruce Stein

[57] ABSTRACT

A process for converting 1,2-saturated 3-keto steroids to 1,2-dehydro steroids which are useful steroid intermediates. The process involves exposing the substrate to steroid-1-dehydrogenase activity in the presence of an added electron carrier and one or more added scavengers of a toxic oxygen species.

17 Claims, No Drawings

MICROBIAL Δ1-DEHYDROGENATION PROCESS USING A SCAVENGER OF TOXIC OXYGEN

BACKGROUND OF THE INVENTION

The first therapeutic use of corticosteroids was demonstrated in the 1950's with the introduction of cortisone acetate treatment for rheumatoid arthritis. Further studies demonstrated that the insertion of unsaturation into the 1,2 position of hydrocortisone and cortisone caused the resultant steroids, prednisolone and prednisone, to have enhanced potency and to cause less drug-induced salt retention. Subsequently, most other steroids used for the treatment of corticoid-responsive diseases have been synthesized so that they contain a double bond in the 1,2 position of the steroid molecule. In 1977, two U.S. patents were issued which represent new approaches to the synthesis of corticosteroids from sterol precursors. U.S. Pat. No. 4,035,236 covers a process for preparing 9α-hydroxyandrostenedione via fermentation of sitosterol, stigmasterol, or cholesterol. U.S. Pat. No. 4,041,055 discloses a general process for the synthesis of medically useful corticosteroids from this androstene. Intermediates covered in this chemistry can possess a 3-keto-$\Delta^{4,9(11)}$ configuration.

Several methods have been described in the literature for microbiological introduction of a 1,2-unsaturated bond in the A-ring of steroid compounds that are important intermediates in the synthesis of medically useful steroids. U.S. Pat. No. 2,837,464 describes the 1-dehydrogenation of steroids by the addition of steroid substrate to fermentation broths of *Arthrobacter simplex*. However, the total utility of this process is limited. This bacterium and other 1-dehydrogenating microorganisms can further degrade certain steroid molecules resulting in a lower final yield as well as undesired side products.

U.S. Pat. No. 3,091,575 discloses an improved method for steroid 1-dehydrogenation by the intermixing of the steroid, an electron carrier, and bacterial cells that have been pretreated with a lower alkanol or lower alkanone such as acetone. This pretreatment reduces one of the undesirable activities, 20-keto reductase activity, in the cells.

U.S. Pat. No. 3,047,469 discloses a different type of a process which comprises subjecting a steroid which is saturated in the 1,2 position to a mixture of an electron carrier and a steroid-1-dehydrogenase containing extract from a microorganism selected from the group consisting of Nocardia, Corynebacterium, Mycobacterium and Cylindrocarpon. This method overcomes several disadvantages encountered by the use of living organisms, including the reduction of accompanying side reactions that lead to steroid degradation.

U.S. Pat. No. 3,091,575 documents a process to eliminate the destruction of the desired product by the addition of inhibitors, such as quinonoid type compounds, to the fermentation broth prior to or at the same time as the addition of the steroid substrate.

The utility of exogenous electron carriers is sometimes limited by the toxic effects that they may exert on the enzyme system (J. H. Quasiel. *Methods in Enzymology.* S. P. Colowick and N. O. Kaplan, Eds, Academic Press, Inc., New York, Vol. 4, pp. 329–336, 1957). Yang and Studebaker (*Biotechnology and Bioengineering*, 20, pp. 17–25, 1978) discussed the potential toxicity of the electron carrier phenazinemethosulfate (PMS) on the steroid-1-dehydrogenase of *Pseudomonas testosteroni* caused by superoxide and peroxide formation. However, they concluded that the 1-dehydrogenase activity was essentially unaffected by the presence of PMS. They suggested that this strict aerobe possessed sufficient superoxide dismutase and catalase activities to remove any superoxide and peroxide that was formed before damage to the steroid 1-dehydrogenase occurred.

The subject invention process represents an improved steroid 1-dehydrogenation bioconversion in the presence of added electron carriers that is not suggested or disclosed by the prior art.

BRIEF SUMMARY OF THE INVENTION

The addition of one or more peroxide scavengers or superoxide dismutases and peroxide scavengers to the microbiological steroid-1-dehydrogenation bioconversions in the presence of an added electron carrier results in a more efficient conversion of 1,2-saturated steroids to their corresponding 1,2-dehydro derivatives than is obtained by the best known prior art process. This addition prevents the deleterious effects of toxic oxygen species, generated by the interaction of the cells and the electron carrier or of the steroid-1-dehydrogenase and the electron carrier, on the steroid-1-dehydrogenase activity. The greater efficiency of this process is manifested by (1) the increase in the quantity of steroid substrate that can be 1-dehydrogenated per gram of dry cell weight; (2) the use of higher substrate levels of certain steroid substrates than is possible in prior art processes; (3) the reduction in the amount of unconverted substrate remaining at the end of the bioconversion reaction; (4) the faster rate of conversion; and, (5) the decrease in the formation of undesirable side products in bioconversions except those conducted with enzyme preparations specifically treated to eliminate the activity of any steroid-degradative enzymes. The net effect is that the subject process gives a better yield of desired product than is obtainable by prior art processes, which results in a more economical process.

DETAILED DESCRIPTION OF THE INVENTION

Microorganism

The microbes which can be used in the subject process are any of the numerous well-known microbes which are known to 1-dehydrogenate steroids and have been described in the prior patent literature for this purpose. Such microbes are listed in Charney, W. and Herzog, H. (1967), *Microbial Transformation of Steroids.* Academic Press, Inc., New York.

Examples of known 1-dehydrogenating microorganisms are species belonging to a wide diversity of procaryotic and eucaryotic genera including Arthrobacter, Corynebacterium, Nocardia, Mycobacterium, Streptomyces, Bacterium, Pseudomonas, Bacillus, Septomyxa, Didymella and Cylindrocarpon.

A bacterium extensively used for the 1-dehydrogenation of steroids is *Arthrobacter simplex*, ATCC 6946, which is disclosed in U.S. Pat. No. 2,837,464. Much of the following will use this microorganism to exemplify the invention process. It should be understood, however, that the subject process also covers the use of any form of microbiological 1-dehydrogenase preparation for steroid bioconversion in the presence of added electron carrier(s) and one or more added inactivators of any toxic oxygen species generated.

Procedure for Preparing the Steroid-1-Dehydrogenase Biocatalyst

The microorganisms are grown in an aqueous nutrient medium containing:

(a) Inorganic compounds such as nitrate or ammonium salts or organic nitrogenous compounds (yeast extract, peptone, cornsteep liquor, etc.) to provide nitrogen for growth.

(b) A carbon and energy source such as carbohydrates and sugar derivatives, oil, fatty acids and their methyl esters, alcohols, amino acids or organic acids.

(c) Ions and trace elements such as sodium, potassium, magnesium, phosphate, sulfate, manganese, copper, cobalt, molybdenum, etc. in levels supplied by tap water or by the less refined medium ingredients (such as cornsteep liquor).

The organisms require oxygen for growth. The temperature range for growth is 10°–45° C. with an optimum of 28°–37° C. for *A. simplex*. The optimum pH for growth of *A. simplex* is around neutrality. The cells are induced for steroid-1-dehydrogenase activity by the addition of a 1,2-saturated 3-keto-steroid compound such as androsta-4-ene-3,17-dione or cortisone acetate, and the like, at a level of 0.005% w/v of the medium or greater. The inducer can be added at any point during the growth cycle. Cultures grown on nutrients such as lard oil usually start synthesizing the steroid-1-dehydrogenase rapidly while cultures grown on glucose require glucose depletion before enzyme synthesis will occur.

After the addition of the inducer, incubation for a period of six or more hours is recommended. The microorganism containing the 1,2-dehydrogenase activity can then be used in any of several forms to catalyze 1-dehydrogenation of the desired steroid substrate. Whole microbial cells can be used directly in the fermentation broth. These same cells can also be used after collection and concentration from the nutrient medium by conventional means such as centrifugation, flocculation and filtration, or ultrafiltration. The isolated cells can be used in a wet state having a moisture content of about 60 to about 85%, or can be dried by treatment with a lower alcohol or alkanone such as acetone, by vacuum-drying with heat, by freeze-drying, by air-drying with heat, or by spray-drying until a moisture content in the range of about 1% to about 30% is reached. A moisture content of about 1% to about 10% is preferred. Cells are preferably stored at 5° C. until used for bioconversions. Active dried cells can also be prepared by immobilizing dried cells by standard techniques, such as entrapment within polyacrylamide gel and collagen or covalent coupling of the cells to a polyelectrolyte carrier as described in *Methods in Enzymology*, Vol. XLIV, pp. 11–317, (1976), Academic Press, Inc., New York. The addition of peroxide scavengers eliminates apparent discrepancies of steroid-1-dehydrogenase activities in cells collected and dried by different methods when these cells are used in different types of bioconversion procedures. Steroid-1-dehydrogenase activity in a cell-free form can be used in soluton or as an immobilized enzyme to catalyze 1-dehydrogenation with similar results. The activity can be released from the microbial cell by conventional techniques, such as sonication or disruption by pressure as described in *Manual of Methods for General Bacteriology*, pp. 367–370, (1981), American Society for Microbiology, Washington, D.C., or by other methods known in the art. The released activity can be used in this form as a crude extract. In addition, further purification can be accomplished using standard biochemical protein purification procedures such as described in *Methods in Enzymology*, Vol. XXII, (1971), Academic Press, Inc., New York. These can include a combination of centrifugation, ammonium sulfate precipitation, gel filtration, ion exchange chromatography, isoelectric processing, and the like.

Bioconversion Process

The bioconversion is accomplished by exposure of the preparation containing steroid-1-dehydrogenase activity to the steroid substrate in the presence of an added electron carrier and one or more added scavengers of toxic oxygen species such as a peroxide scavenger or a superoxide dismutase and a peroxide scavenger and the like. The bioconversion can be performed in an aqueous system or in a mixed system containing greater than zero, but less than 100% water-immiscible organic solvent, for example, toluene, xylene, benzene, heptane, butyl acetate, methylene chloride, and the like. The exogenous electron carrier is added, advantageously, to stimulate the steroid-1-dehydrogenation and/or to prevent steroid-degrading activities in preparations where these activities have not been previously eliminated.

Examples of useful exogenous electron carriers are menadione (2-methyl-1,4-naphthoquinone), menadione bisulfite, 1,4-naphthoquinone, phenazine methosulfate, phenazine ethosulfate, vitamim K-type compounds, and the like. The electron carrier, advantageously, is added in catalytic amounts, for example, about $2.5 \times 10^{-4}$ M to about $5.0 \times 10^{-3}$ M, to improve the 1-dehydrogenation reaction. The addition of toxic oxygen species scavengers causes beneficial effects to be realized when an increased level of the added electron carrier is used. These effects may include the use of less steroid-1-dehydrogenase to convert a specific amount of steroid, better long-term reaction rates, lower final residuals, the use of higher substrate levels and the like. If the scavenger is omitted, the use of a higher concentration of electron carrier can affect the reaction in a deleterious manner.

Scavengers of toxic oxygen species are, advantageously, added to the bioconversion mixture at the beginning of the reaction. The scavengers may act by elimination of the harmful oxygen species or may render the harmful oxygen species less active in attacking enzymes by stabilizing that species. Harmful oxygen species may include hydrogen peroxide, superoxide anion, hydroxyl radical, singlet oxygen and the like. The scavenger can be of an organic nature, for example, the enzymes catalase, peroxidase, and superoxide dismutase, or the toxic oxygen species stabilizers mannitol, α-tocopherol (vitamin E), urea, an quinine sulfate; or can be of an inorganic nature such platinum and other metal catalysts. The scavenger used and the preferred level of use can be determined by economic consideration. Catalase can be used in the range of about 100 to about 10,000 units per gram of steroid converted. One unit is described as the amount of enzyme that will decompose 1 μmole of $H_2O_2$ per minute at pH 7 at 25° C. while the $H_2O_2$ concentration falls from 10.3 to 9.2 μmoles/ml of reaction mixture.

The reaction mixtures used to 1-dehydrogenate steroids are incubated 0–7 days at a temperature range of 5°–45° C. During incubation, the mixture has access to molecular oxygen and is preferably stirred. The rate of 1-dehydrogenation typically decreases with time. The bioconversion can proceed to 90–100% of completion in less than 2 days using substrate levels in the range of about 5 to about 60 g/liter. The substrate:cell level can vary from about 2 to about 25 g substrate per gram of dry cell weight.

Compounds that are useful in the practice of this invention belong to the 3-keto-$\Delta^4$-androstene and 3-keto-$\Delta^4$-pregnene series of steroids. It is recognized that steroid substrates for the steroid-1-dehydrogenase will have saturation between carbons C1 and C2 of the A-ring, and will have a hydroxyl or keto group at position 3 on the A-ring. Members of the androstene series include:

(1) androst-4-ene-3,17-dione and
(2) androst-4,9(11)-diene-3,17-dione, 11-hydroxyandrost-4-ene-3,17-dione and their 6α-fluoro,6α-methyl, or 16-methyl derivatives.

Among the steroids of the 3-keto-$\Delta^4$-pregnene series which can be used are:

1. 17α-hydroxypregn-4-ene-20-yn-3-one and its 16-methyl derivatives;
2. 11β,21-dihydroxy-pregn-4,17(20)-diene-3-one and its 6α-methyl derivative;
3. 20-chloro-pregn-4,9(11),17(20)-triene-21-al-3-one;
4. several groups of 3,20-diketo-$\Delta^4$-pregnenes, including
    (a) 11,17,21-trihydroxy compounds, such as hydrocortisone and its 6α-methyl derivative;
    (b) 9β,11β-epoxy-17,21-dihydroxy compounds, such as 9β,11β-epoxy-17,21-dihydroxy-16β-methyl-pregn-4-ene-3,20-dione;
    (c) 3,20-diketo-4,9(11)-pregnedienes such as 17α,21-dihydroxy-pregn-4,9(11)-diene-3,20-dione and its 16α-methyl, 16β-methyl or 16α-hydroxy derivatives or 17α-acetate ester;
    (d) 3,20-diketo-4,9(11), 16-pregnetrienes, such as 21-hydroxy-pregn-4,9(11), 16-triene-3,20-dione and its 6α-fluoro derivative.

The 21-ester derivatives of those steroids containing a 21-hydroxyl group (#2 and #4) serve as substrates also. The preferred 21-esters consist of lower alkyl or aryl groups such a lower fatty acids, e.g., acetic acid and monocyclic carboxylic acids, e.g., benzoic acid.

The type of procedure to be used for the bioconversion and the appropriate levels of enzyme preparation, steroid substrate, electron acceptor and peroxide scavenger vary dependent on the nature of the steroid molecule to be dehydrogenated and can be determined by one skilled in the art. The following are provided as general examples of the various bioconversion procedures that can be used to 1-dehydrogenate steroids efficiently in the presence of an added electron carrier and one or more added scavengers of toxic oxygen species.

Fermentation Bioconversion

After substantial cell growth and steroid-1-dehydrogenase induction have occurred, the scavenger of a toxic oxygen species, electron carrier, and steroid substrate are added to the fermentor. The electron carrier can be added to stimulate 1-dehydrogenase activity and prevent steroid degradation or can be added to inhibit degradation of the steroid to undesired products for bioconversions that do not require the carrier for steroid-1-dehydrogenase activity. The steroid and/or electron carrier can be added as dry powders, aqueous slurries, solutions or slurries in a water-miscible solvent, for example, ethanol, methanol, dimethylformamide, dimethylsulfoxide, acetone, and the like. The preferred electron carrier for *A. simplex* catalyzed fermentation conversions is a naphthoquinone, for example, 2-methyl-1,4-naphthoquinone, added in catalytic amounts. The steroid level can vary from about 5 to about 50 grams per liter. The percent of unconverted substrate at the end of the reaction will increase as the substrate level increases. The optimum level is determined, in part, by the amount of starting substrate that can be tolerated in the product when it is used in subsequent chemical steps. Foaming characteristics of the mixture of steroid and the fermentation broth also help determine the optimum substrate concentrations. Antifoam or defoaming agents, for example, lard oil, silicones and polyalkylene glycols can be added to aid in control of the foams and to aid in steroid suspension.

Bioconversions in an Aqueous System Using Isolated Preparations

The preparation possessing steroid-1-dehydrogenase activity, the steroid, the electron carrier, and the scavenger are suspended in a buffered aqueous solution of about 0.01M to about 2M with a pH in the range of pH 6 to pH 10. The order of addition of the constituents can vary without adversely affecting the reaction. The active preparation can be isolated wet cells, dried cells, immobilized cells, or a cell-free enzyme system. The amount of cell equivalents can range from about 0.1 to about 50 g. dry weight/liter. The steroid is added at a weight ratio of about 0.05 to about 15 (steroid:cells). Cells levels of about 2.0 g. to about 25 g. with about 15–50 g/liter steroid are preferred. The steroid substrate can be added as a dry powder, an aqueous slurry, or dissolved (or suspended) in a water-miscible organic solvent such as dimethylformamide, dimethylsulfoxide, ethanol, methanol, acetone, and the like, (not greater than 5% of final volume). Surfactants, for example Tween 80, can be added in low concentration, for example, about 0.5 to about 5%, to aid in steroid suspension. The electron carrier, e.g., menadione, 1,4-naphthoquinone, phenazine methosulfate, can be added as a powder, an aqueous slurry, or dissolved in a water-miscible organic solvent. The scavengers of the toxic oxygen species are preferably added at the initiation of the reaction. The degree of improvement observed by this process is significantly affected by the type of enzyme preparation used, the substrate:cell ratio (preferably about 2:1 or greater), and/or the level of electron carrier used as catalyst.

Bioconversions in the Presence of a Water-Immiscible Solvent

A water-immiscible solvent can be added to the hydrated steroid-1-dehydrogenase activity along with the steroid substrate, electron carrier and a scavenger of the toxic oxygen species. This solvent can be added at a level sufficient to dissolve part or all of the steroid substrate and product. This modification can be employed in the fermentation broth, with isolated wet cells, immobilized cells, cell-free enzyme or immobilized enzyme. The reaction rate for bioconversions carried out in the presence of a water-immiscible solvent is a strong function of the agitation power; therefore the bioconversion mixture should be mixed with as high an agitation power as is possible.

Bioconversion products and unconverted substrate can be recovered from the previously described mixtures by conventional means. Steroids are typically recovered by filtration, followed by extraction of the filter cake with an organic solvent, such as acetone or methylene chloride. Alternatively, the whole bioconversion mixture can be extracted by mixing with a water-immiscible solvent such as butyl acetate or methylene chloride. The product is then isolated from the organic solvent.

The utility of 1,2-dehydro steroids is well known. For example, U.S. Pat. No. 3,284,447 discloses the utility of $\Delta^{1,4,9(11)}$ pregnetrienes in the synthesis of diurectic corticosteroids substituted at carbon 16. U.S. Pat. No. 4,041,055 discloses a process for the synthesis of corticosteroids from $\Delta^{1,4}$-androstenedione and other important intermediates in the production of medically useful steroids.

The following are specific examples which demonstrate the superiority of the invention process over prior art processes.

EXAMPLE 1

Fermentation bioconversion of androst-4,9(11)-diene-3,17-dione by *A. simplex*

(a) Preparation of biocatalyst: *Arthrobacter simplex* (ATCC 6946) is grown in a medium containing 20 g/l. cornsteep liquor and 15 g/l. lard oil #2, pH 7.0. After incubation on a rotary shaker for 2 days at 28°20 C., cortisone acetate (0.15 g/l.) is added to induce steroid-1-dehydrogenase activity.

(b) Bioconversion—The following day, androst-4,9(11)-diene-3,17-dione is added to the flasks at various levels. Menadione and/or catalase additions are made to certain flasks. The bioconversions are monitored by thin layer chromatography of methylene chloride extracts. The bioconversion mixtures that contain only steroid at 3.5 g/liter show poor 1-dehydrogenation. After one day of incubation, approximately 10% of the substrate has been converted to the 1,2-dehydro product and about 5% to other products. By the fourth day, less than 5% of the 1,2-dehydro product remains with about 10 to 20% of the steroid appearing as 3 or more undesirable polar steroid products. The bioconversion mixtures that contain the steroid substrate (3.5 g/l.) and menadione ($5 \times 10^{-4}$M) accumulate about 50% of the total steroid present as the 1-dehydrogenated product. However, the reaction does not proceed to completion with further incubation and further degradation of the steroid is observed, but to a lesser extent. Successful conversion is observed in bioconversion mixtures that contain catalase (10 mg/l., Sigma product C-10 equivalent to 16,000 units/liter, menadione ($5 \times 10^{-4}$M), and substrate (10 g/liter). The conversion is about 83% complete in 22 hours and about 95% complete in 46 hours. No significant degradation products are detectable by tlc during this reaction. The control containing catalase and steroid exhibits a conversion similar to that of the mixture comprised of the fermentation broth and steroid.

EXAMPLE 2

Fermentation bioconversion of 11β-hydroxy-androstenedione(11βOH-AD) by *A. simplex*

(a) Preparation of biocatalyst: *Arthrobacter simplex* (ATCC 6946) is grown in shake flasks in a medium containing glucose, cornsteep liquor and Bactopeptone (Difco) at 6 g/liter each pH 7.0. The cultures are incubated at 28° C. on a rotary shaker until glucose depletion occurs. At that time, cortisone acetate (0.1 g/liter) is added to induce steroid-1-dehydrogenase synthesis.

(b) Bioconversion: After overnight incubation, the steroid 11βOH-AD is added to each flask at a level of 10 grams/liter. The control flask receives no further additions. Menadione ($5 \times 10^{-4}$M) and catalase (10 mg/liter, Sigma product C-10 equivalent to 16,000 units/liter), are added to the experimental flask. The bioconversion mixtures are incubated on a rotary shaker at 28° C. The bioconversions are monitored by extracting a sample of a known volume with two times that volume of methylene chloride. A sample of the methylene chloride extract is subjected to thin layer chromatography in an ethyl acetate:heptane (1:1) system. The progress of the conversion is estimated by comparison to appropriate steroid standards.

Results

| Flask | Bioconversion hrs. | Unconverted % Substrate | Comments |
|---|---|---|---|
| Control | 24 | about 3% | Minor levels of accumulated degradation products. |
|  | 48 | about 2% | Detectable loss of steroid. |
|  | 5 days | about 2% | ~50% loss of steroid detected. |
| Experiment: menadione & catalase | 24 | about 5% |  |
|  | 48 | about 5% |  |
|  | 5 days | about 5% | No detected steroid degradation. |

EXAMPLE 3

Preparation of dried cells: *Arthrobacter simplex* (ATCC 6946) is inoculated into shake flasks containing a medium of cerelose, peptone, and cornsteep liquor (6 g/l. of each) pH 7.0. The cultures are incubated on a rotary shaker at 28° C. unitl glucose exhaustion occurs. Cortisone acetate (0.5 g/l.) is added at that time and the flasks are incubated an additional 16 hrs. The cells are harvested by centrifugation, washed twice with water then placed in an oven under reduced pressure at 45° C. until dry.

Bioconversion of Hydrocortisone to Prednisolone

Dried cells are resuspended in 50 mM phosphate buffer to a concentration of 0.05 g/l. in a 500 ml Erlenmeyer flask. The substrate is added as a dimethylformamide (DMF) solution (100 mg hydrocortisone/ml. DMF) to a final bioconversion concentration of 0.5 g/l. Menadione is added to the flasks as an ethanolic solution (8.6 mg/ml. ethanol) at a level of 0.5 ml per 100 ml of final reaction mixture. The final volume of the reaction mixture in all flasks is 100 ml with all adjustments to volume made by the addition of 50 mM phosphate buffer. Catalase may be purchased from the Sigma Chemical Company and the enzyme activity of this preparation is 2300 units/mg.

Catalase (2300 units) is added to flask A and compared to flask B which does not contain this enzyme, this being the only difference between the two bioconversions. The mixtures are incubated at 28° C. with agitation. After 23 hours of incubation, about 69% of the hydrocortisone in flask A is bioconverted to prednisolone. In the same time period only about 42% of the hydrocortisone in flask B is converted to prednisolone. The results show that the addition of the enzyme catalase, improves the bioconversion process by an approximate 27% increase in product produced. The prednisolone is recovered by conventional means. *Bacterium cyclooxydans* ATCC 12673, which is disclosed in U.S. Pat. No. 3,065,146 can be substituted for *Arthrobacter simplex* in this example with comparable results.

EXAMPLE 4

Cells are grown as described in Example 1. The active cells are harvested by centrifugation or by filtration in the presence of filter aid. The wet cell cakes are heat-dried to a moisture content of about 3 to about 5%. The dried cells are resuspended in 50 mM potassium phosphate buffer pH 7.5 and stirred for 20 minutes then distributed in 100 ml portions in 500 ml Erlenmeyer flasks. Menadione is added as an ethanolic solution to give a final concentration of $5 \times 10^{-4}$M. Catalase is added to one-half the flasks at a level of 10 mg/liter, about 16,000 units/liter. Androst-4,9(11)-diene-3,17-dione (10 g/l.) is added as a dry powder. The flasks are incubated at 28° C. on a rotary shaker. Samples of the bioconversion mixtures are extracted with methylene chloride. Dried extracts are assayed by gas chromatography to determine reaction progress.

Results

| Dried Cake Equivalents g/liter | Cell Type | Catalase | % Unconverted Substrate Remaining at 26 Hours |
|---|---|---|---|
| 5 | Centrifuged | − | 38.9 |
| | | + | 9.8 |
| | Filtered | − | 47.4 |
| | | + | 8.3 |
| 7.5 | Centrifuged | − | 24.0 |
| | | + | 9.3 |
| | Filtered | − | 39.9 |
| | | + | 7.2 |
| 10.0 | Centrifuged | − | 9.8 |
| | | + | 9.8 |
| | Filtered | − | 31.9 |
| | | + | 7.0 |

EXAMPLE 5

Dried *A. simplex* cells are resuspended in 50 mM potassium phosphate buffer, pH 7.5 at a level of 5 g dried centrifuged cake/liter for 20 minutes; 100 ml portions of the cell suspension are placed in 500 ml Erlenmeyer flasks. Menadione and catalase are added to flasks as indicated in the following table. 16β-Methylandrost-4,9(11)-diene-3,17-dione is added to the flasks as a micronized powder at a level of 15 g/liter. The flasks are incubated on a rotary shaker at 31° C. Samples are extracted with methylene chloride. These extracts are analyzed by gas chromatography for steroid content.

Results

| Catalase Level mg/liter | Menadione mg/liter | % Unconverted Substrate | | |
|---|---|---|---|---|
| | | 19 hr. | 43 hr. | 91 hr. (Harvest) |
| 2.5 (4000 units/l.) | 86 | 24.3 | 12.0 | 9.5 |
| 2.5 (4000 units/l.) | 129 | 22.1 | 15.0 | 12.7 |
| 5.0 (8000 units/l.) | 86 | 21.9 | 9.9 | 8.3 |
| 5.0 (8000 units/l.) | 129 | 14.6 | 4.6 | 4.2 |

EXAMPLE 6

Dried *A. simplex* cells are resuspended and distributed into flasks as described in Example 4. The final cell level is equivalent to about 1.5 g dried cell cake/liter. Five milligrams of catalase (8000 units) are added to each flask. Eight and six-tenth milligrams of menadione are added to each flask as an ethanolic solution. Substrate (16β-methyl-$\Delta^{9,11}$-androstenedione) is added in as a dry powder to give a level of 20 g/liter. Superoxide dismutase (Sigma product S8254 with about 3000 units/mg protein) is added to one flask at a level of 3 mg/liter. The other flask has no superoxide dismutase addition. The flasks are incubated at 31° C. on a rotary shaker. Samples are taken at regular intervals, extracted with methylene chloride and assayed for bioconversion progress.

Results

| Flask | Superoxide Dismutase Addition (mg/flask) | Amount of Product Formed | |
|---|---|---|---|
| | | 22 hrs. | 70 hrs. |
| 1 | 0 | .37 g | .68 g |
| 2 | 0.3 mg | .41 g | .81 g |

EXAMPLE 7

The following materials are combined in a reaction vessel (1 liter basis):
(a) 0.68 l. of 50 mM KPO$_4$ buffer, pH=7.5
(b) 6.4 gm of dry *A. simplex* cells
(c) 0.32 gm of menadione
(d) 13 mg of bovine liver catalase (2000 I.U./mg)
(e) 32 gm of androst-4,9(11)-diene-3,17dione
(f) 0.320 l. of toluene.

The reaction mixture is agitated at 15 cal./l. minute. Air is added to the reaction vessel as necessary to maintain the oxygen level in gas space of the reactor above 3%. The temperature is controlled at 28° C.±1° C. The reaction is conducted for 47 hrs, at which time the toluene phase is collected from the bioconversion mixture. For this example, the steroid composition in the toluene phase is about 99.9% product (androst-1,4,9(11)-triene-3,17-dione) and 0.1% unconverted substrate (androst-4,9-(11)-diene-3,17-dione).

EXAMPLE 8

The following materials are combined in 3 separate shake flasks:
(a) 23 ml of 50 mM KPO$_4$ buffer, pH=7.5
(b) 0.04 gm of dry *A. simplex* cells
(c) 0.25 ml of 50 mM menadione in 3A-alcohol.
The following additions are made to these mixtures:
Shake flask #1—nothing
Shake flask #2—0.167 mg catalase (2000 I.U./mg.)
Shake flask #3—2 mg of 5% platinum on carbon.

Androst-4,9(11)-diene-3,17-dione (0.2 gm) and 2 ml of toluene are added to each flask. The flasks are agitated for 3 days at room temperature.

After 3 days of incubation, 23 ml of toluene are combined with the contents of each flask. The extracts are collected and analyzed.

|  | Shake Flask #1 Control | #2 With Catalase | #3 With Platinum |
| --- | --- | --- | --- |
| Product (Androst-1,4,9(11)-triene-3,17-dione) | 80.8% | 99.9% | 95.9% |
| Substrate (Androst-4,9(11)-diene-3,17-dione) | 19.2% | 0.1% | 4.1% |

EXAMPLE 9

*Arthrobacter simplex* cells are grown in a medium containing 20 g/l. cornsteep liquor and 15 g/l. lard oil, pH 7.0. The culture is incubated at 28° C. for about 26 hours, cortisone acetate is added at a level of 0.15 g/liter. Incubation is continued for about 18 hours. The cells are separated from the fermentation broth by centrifugation. The obtained cell pellet is resuspended in 0.05M potassium phosphate buffer, pH 7.5, to one-half its original concentration in the fermentation broth. The steroid substrate, androst-4,9(11)-dione-3,20-dione, is added to the flasks as a dry powder at a level of 10 g/liter. One flask (A) has no further additions. The other (B) receives 8.6 mg of menadione and 1600 units of catalase in addition to the steroid. After 5 hours of incubation, Flask A has about 5% of the 1,2-dehydro product accumulated. The steroid in Flask B consists of a mixture of about 95% of the 1,2-dehydro product and about 5% unconverted substrate. Continued incubation of Flask A results in accumulation of about 10% of the 1,2-dehydro product and detectable levels of other undesired degradation products. Continued incubation of Flask B does not result in the formation of any more product, however, no detectable degradation products are observed.

EXAMPLE 10

By substituting the following list of substrates for hydrocortisone in Example 3, or androst-4,9(11)-diene-3,17-dione in Example 1 or 7 or 9, or 16β-methyl-Δ$^{4,9,11}$-androstenedione in Example 6, there are obtained the corresponding listed products:

Substrates 1. androst-4-ene-3,17-dione
2. 6α-fluoro-androst-4,9(11)-diene-3,17-dione
3. 6α-methyl-androst-4,9(11)-diene-3,17-dione
4. 16β-methyl-androst-4,9(11)-diene-3,17-dione
5. 17α-hydroxypregn-4-ene-20-yn-3-one
6. 17α-hydroxypregn-4,9(11)-diene-20-yn-3-one
7. 17α-hydroxy-16β-methyl-pregn-4,9(11)-diene-20-yn-3-one
8. 11β,21-dihydroxy-pregn-4,17(20)-diene-3-one
9. 21-acetoxy-11β-hydroxy-pregn-4,17(20)-diene-3-one
10. 6α-methyl-11β,21-dihydroxy-pregn-4,17(20)-diene-3-one
11. 20-chloro-pregn-4,9(11),17(20)-triene-21-al-3-one
12. hydrocortisone
13. 6α-methyl hydrocortisone
14. 21-acetoxy-11β,17-dihydroxy-16β-methyl-pregn-4-ene-3,20-dione
15. 21-acetoxy-9α-fluoro-11β,17-dihydroxy-16β-methyl-pregn-4-ene-3,20-dione
16. 21-acetoxy-9β,11β-epoxy-17-hydroxy-16β-methyl-pregn-4-ene-3,20-dione
17. 21-acetoxy-17-hydroxy-pregn-4,9(11)-diene-3,20-dione
18. 21-acetoxy-16α,17-dihydroxy-pregn-4,9(11)-diene-3,20-dione
19. 21-acetoxy-17-hydroxy-16α-methyl-pregn-4,9(11)-diene-3,20-dione
20. 21-benzoyloxy-17-hydroxy-16β-methyl-pregn-4,9(11)-diene-3,20-dione
21. 21-acetoxy-17-hydroxy-16β-methyl-pregn-4,9(11)-diene-3,20-dione
22. 21-acetoxy-pregn-4,9(11),16-triene-3,20-dione
23. 21-acetoxy-6α-fluoro-pregn-4,9(11),16-triene-3,20-dione
24. 21-acetoxy-9α-fluoro-11β,16α,17-trihydroxy-pregn-4-ene-3,20-dione
25. 21-acetoxy-6α,9α-difluoro-11β,16α,17-trihydroxy-pregn-4-ene-3,20-dione-16,17-acetonide
26. 21-acetoxy-6α-fluoro-11β-hydroxy-16α-methyl-pregn-4-ene-3,20-dione
27. 21-acetoxy-6α-fluoro-11β,17-dihydroxy-pregn-4-ene-3,20-dione
28. 21-acetoxy-6α,9α-difluoro-11β,17-dihydroxy-16α-methyl-pregn-4-ene-3,20-dione
29. 21-acetoxy-9α-fluoro-11β,16α,17-trihydroxy-pregn-4-ene-3,20-dione-16,17-acetonide
30. 21-acetoxy-9β,11β-epoxy-6α-fluoro-16α,17-dihydroxy-pregn-4-ene-3,20-dione-16,17-acetonide
31. 21-acetoxy-9β,11β-epoxy-16α-hydroxy-pregn-4-ene-3,20-dione
32. 21-acetoxy-9β,11β-epoxy-16α,17-dihydroxy-pregn-4-ene-3,20-dione-16,17-acetonide.

Products 1a. androst-1,4-diene-3,17-dione
2a. 6α-fluoro-androst-1,4,9(11)-triene-3,17-dione
3a. 6α-methyl-androst-1,4,9(11)-triene-3,17-dione
4a. 16β-methyl-androst-1,4,9(11)-triene-3,17-dione
5a. 17α-hydroxypregn-1,4-diene-20-yn-3-one
6a. 17α-hydroxypregn-1,4,9(11)-triene-20-yn-3-one
7a. 17α-hydroxy-16β-methyl-pregn-1,4,9(11)-triene-20-yn-3-one
8a. 11β,21-dihydroxy-pregn-1,4,17(20)-triene-3-one
9a. 21-acetoxy-11β-hydroxy-pregn-1,4,17(20)-triene-3-one and 11β,21-dihydroxy-pregn-1,4,17(20)-triene-3-one
10a. 6α-methyl-11β,21-dihydroxy-pregn-1,4,17(20)-triene-3-one
11a. 20-chloro-pregn-1,4,9(11),17(20)-tetraene-21-al-3-one
12a. prednisolone
13b. 6α-methyl-prednisolone
14a. 21-acetoxy-11β,17-dihydroxy-16β-methyl-pregn-1,4-diene-3,20-dione and 11β,17,21-trihydroxy-16β-methyl-pregn-1,4-diene-3,20-dione
15a. 21-acetoxy-9α-fluoro-11β,17-dihydroxy-16β-methyl-pregn-1,4-diene-3,20-dione and 9α-fluoro-11β,17,21-trihydroxy-16β-methyl-pregn-1,4-diene-3,20-dione
16a. 21-acetoxy-9β,11β-epoxy-17-hydroxy-16β-methyl-pregn-1,4-diene-3,20-dione and 9β,11β-epoxy-17,21-dihydroxy-16β-methyl-pregn-1,4-diene-3,20-dione 17a. 21-acetoxy-17-hydroxy-pregn-1,4,9(11)-triene-3,20-dione and 17,21-dihydroxy-pregn-1,4,9(11)-triene-3,20-dione
18a. 21-acetoxy-16α,17-dihydroxy-pregn-1,4,9(11)-triene-3,20-dione and 16α,17,21-trihydroxy-pregn-1,4,9(11)-triene-3,20-dione
19a. 21-acetoxy-17-hydroxy-16α-methyl-pregn-1,4,9(11)-triene-3,20-dione and 17,21-dihydroxy-16α-methyl-pregn-1,4,9(11)-triene-3,20-dione
20a. 21-benzoyloxy-17-hydroxy-16β-methyl-pregn-1,4,9-(11)-triene-3,20-dione
21a. 21-acetoxy-17-hydroxy-16β-methyl-pregn-1,4,9(11)-triene-3,20-dione and 17,21-dihydroxy-16β-methyl-pregn-1,4,9(11)-triene-3,20-dione
22a. 21-acetoxy-pregn-1,4,9(11),16-tetraene-3,20-dione and 21-hydroxy-pregn-1,4,9(11),16-tetraene-3,20-dione
23a. 21-acetoxy-6α-fluoro-pregn-1,4,9(11),16-tetraene-3,20-dione and 6α-fluoro-21-hydroxy-pregn-1,4,9(11),16-tetraene-3,20-dione
24a. 21-acetoxy-9α-fluoro-11β,16α,17-trihydroxy-pregn-1,4-diene-3,20-dione and 9α-fluoro-11β,16α,17,21-tetrahydroxy-pregn-1,4-diene-3,20-dione
25a. 21-acetoxy-6α,9α-difluoro-11β,16α,17-trihydroxy-pregn-1,4-diene-3,20-dione-16,17-acetonide and 6α,9α-fluoro-11β,16α,17,21-tetrahydroxy-pregn-1,4-diene-3,20-diene-16,17-acetonide
26a. 21-acetoxy-6α-fluoro-11β-hydroxy-16α-methyl-pregn-1,4-diene-3,20-dione and 6α-fluoro-11β,21-dihydroxy-16α-methyl-pregn-1,4-diene-3,20-dione
27a. 21-acetoxy-6α-fluoro-11β,17-hydroxy-pregn-1,4-diene-3,20-dione and 6α-fluoro-11β,17,21-trihydroxy-1,4-diene-3,20-dione
28a. 21-acetoxy-6α,9α-difluoro-11β,17-dihydroxy-16α-methyl-pregn-1,4-diene-3,20-dione and 6α,9α-difluoro-11β,17,21-trihydroxy-1,4-diene-3,20-dione
29a. 21-acetoxy-9α-fluoro-11β,16α,17-trihydroxy-pregn-1,4-diene-3,20-dione-16,17-acetonide
30a. 21-acetoxy-9β,11β-epoxy-6α-fluoro-16α,17-dihydroxy-pregn-1,4-diene-3,20-dione-16,17-acetonide
31a. 21-acetoxy-9β,11β-epoxy-16-hydroxy-pregn-1,4-diene-3,20-dione and 9β,11β-epoxy-16α,21-dihydroxy-pregn-1,4-diene-3,20-dione
32a. 21-acetoxy-9β,11β-epoxy-16α,17-dihydroxy-pregn-1,4-diene-3,20-dione-16,17-acetonide.

Other substrates and products are as follows:

Substrate→Product (1) 11β-hydroxy-16β-methyl-androst-4-ene-3,17-dione→11β-hydroxy-16β-methyl-androst-1,4-diene-3,17-dione
(2) 11β-hydroxy-16α-methyl-androst-4-ene-3,17-dione→11β-hydroxy-16α-methyl-androst-1,4-diene-3,17-dione
(3) 6α-fluoro-11β-hydroxy-androst-4-ene-3,17-dione→6α-fluoro-11β-hydroxy-androst-1,4-diene-3,17-dione
(4) 6α-methyl-11β-hydroxy-androst-4-ene-3,17-dione→6α-methyl-11β-hydroxy-androst-1,4-diene-3,17-dione
(5) 11α-hydroxy-androst-4-ene-3,17-dione→11α-hydroxy-androst-1,4-diene-3,17-dione
(6) androst-4-ene-3,11,17-trione→androst-1,4-diene-3,11,17-trione.

What is claimed is:

1. A process for converting 1,2-saturated 3-keto steroids to 1,2-dehydro 3-keto steroids which comprises exposing 1,2-saturated 3-keto steroids to a preparation containing steroid-1-dehydrogenase activity from *Arthrobacter simplex* or *Bacterium cyclooxydans* in the presence of an added electron carrier and one or more added scavengers of a toxic oxygen species selected from the group consisting of catalase, superoxide dismutase and platinum.

2. A process, according to claim 1, wherein said toxic oxygen species is hydrogen peroxide.

3. A process, according to claim 1, wherein said added scavenger of toxic oxygen species is catalase.

4. A process, according to claim 1, wherein said added scavenger of toxic oxygen species is platinum.

5. A process, according to claim 1, wherein said toxic oxygen species are superoxide and peroxide.

6. A process according to claim 1 where said added scavenger of toxic oxygen species is superoxide dismutase.

7. A process, according to claim 1, wherein said electron carrier is selected from the group comprised of menadione, phenazine methosulfate, phenazine ethosulfate, dichlorophenol indophenol, 1,4-naphthoquinone, menadione bisulfite, ubiquinones (Coenzyme Q) or vitamin K-type compounds.

8. A process, according to claim 1, wherein said 1,2-saturated 3-keto steroid is a 1,2-saturated 3-keto androstene and is selected from the group consisting of:
androst-4-ene-3,17-dione;
6α-fluoro-androst-4,9(11)-diene-3,17-dione;
6α-methyl-androst-4,9(11)-diene-3,17-dione;
16β-methyl-androst-4,9(11)-dione-3,17-dione;
androst-4,9(11)-diene-3,17-dione;
11β-hydroxy-androst-4-ene-3,17-dione;
11β-hydroxy-16β-methyl-androst-4-ene-3,17-dione;
6α-fluoro-11β-hydroxy-androst-4-ene-3,17-dione;
11β-hydroxy-6α-methyl-androst-4-ene-3,17-dione;
11α-hydroxy-androst-4-ene-3,17-dione; and,
androst-4-ene-3,11,17-trione.

9. A process, according to claim 1, wherein said 1,2-saturated 3-keto steroid is a 1,2-saturated 3-keto pregnene and is selected from the group consisting of:
17α-hydroxypregn-4-ene-20-yn-3-one;
17α-hydroxypregn-4,9(11)-diene-20-yn-3-one;
17α-hydroxy-16β-methyl-pregn-4,9(11)-diene-20-yn-3-one;
11β,21-dihydroxy-pregn-4,17(20)-diene-3-one;
21-acetoxy-11β-hydroxy-pregn-4,17(20)-diene-3-one;
6α-methyl-11β,21-dihydroxy-pregn-4,17(20)-diene-3-one;
20-chloro-pregn-4,9(11),17(20)-triene-21-al-3-one;
hydrocortisone;
6α-methyl hydrocortisone;
21-acetoxy-11β,17-dihydroxy-16β-methyl-pregn-4-ene-3,20-dione;
21-acetoxy-9α-fluoro-11β,17-dihydroxy-16β-methyl-pregn-4-ene-3,20-dione;
21-acetoxy-9β,11β-epoxy-17-hydroxy-16β-methyl-pregn-4-ene-3,20-dione;
21-acetoxy-17-hydroxy-pregn-4,9(11)-diene-3,20-dione;
21-acetoxy-16α,17-dihydroxy-pregn-4,9(11)-diene-3,20-dione;
21-acetoxy-17-hydroxy-16α-methyl-pregn-4,9(11)-diene-3,20-dione;
21-benzoyloxy-17-hydroxy-16β-methyl-pregn-4,9(11)-diene-3,20-dione;
21-acetoxy-17-hydroxy-16β-methyl-pregn-4,9(11)-diene-3,20-dione;

21-acetoxy-pregn-4,9(11),16-triene-3,20-dione;
21-acetoxy-6α-fluoro-pregn-4,9(11),16-triene-3,20-dione;
21-acetoxy-9β,11β-epoxy-6α-fluoro-16α,17-dihydroxy-pregn-4-ene-3,20-dione-16,17-acetonide;
21-acetoxy-9β,11β-epoxy-16α-hydroxy-pregn-4-ene-3,20-dione;
21-acetoxy-9β,11β-epoxy-16α,17-dihydroxy-pregn-4-ene-3,20-dione-16,17-acetonide;
21-acetoxy-9α-fluoro-11β,16α,17-trihydroxy-pregn-4-ene-3,20-dione;
21-acetoxy-6α,9α-difluoro-11β,16α,17-trihydroxy-pregn-4-ene-3,20-dione-16,17-acetonide;
21-acetoxy-6α-fluoro-11β-hydroxy-16α-methyl-pregn-4-ene-3,20-dione;
21-acetoxy-11β,17-dihydroxy-pregn-4-ene-3,20-dione;
21-acetoxy-6α,9α-difluoro-11β,17-dihydroxy-16α-methyl-pregn-4-ene-3,20-dione; and,
21-acetoxy-9α-fluoro-11β,16α,17-trihydroxy-pregn-4-ene-3,20-dione-6,17-acetonide.

10. A process, according to claim 1, wherein said steroid-1-dehydrogenase activity is prepared from *Arthrobacter simplex*.

11. A process, according to claim 1, wherein said steroid-1-dehydrogenase activity is prepared from *Bacterium cyclooxidans*.

12. A process, according to claim 1, wherein said preparation containing steroid-1-dehydrogenase activity is a fermentation broth.

13. A process, according to claim 1, wherein said preparation containing steroid-1-dehydrogenase activity is a wet cell paste or cake having a moisture content of about 60% to about 85%.

14. A process, according to claim 1, wherein said preparation containing steroid-1-dehydrogenase activity is a dried cell cake having a moisture content of about 1% to about 30%.

15. A process, according to claim 1, wherein said exposure is carried out in a buffered aqueous system having a molarity of about 0.01M to about 2.0M.

16. A process, according to claim 1, wherein said exposure is carried out in a system comprised of an aqueous solution and a water-immiscible solvent.

17. A process, according to claim 16, wherein said water-immiscible solvent contains toluene, xylene or benzene.

* * * * *

UNITED STATES PATENT OFFICE
CERTIFICATE OF CORRECTION

Patent No. 4,749,649   Dated June 7, 1988

Inventor(s) Evans et al.

It is certified that error appears in the above-identified patent and that said Letters Patent are hereby corrected as shown below:

Title page (title): "Microbial Δ1-"should read -- Microbial $\Delta_1^1$--.
Column 1, (title): "Microbial Δ1-"should read -- Microbial $\Delta^1$--.
Column 4, line 56: "an"should read --and--.
Column 7, lines 29-30: "2820C."should read --28°C.--.
Column 8, line 47: "unitl"should read --until--.
Column 13, line 62: "11αhy"should read --11α-hy--.

Signed and Sealed this

Seventh Day of February, 1989

Attest:

DONALD J. QUIGG

*Attesting Officer*   *Commissioner of Patents and Trademarks*